United States Patent
Joseph et al.

(10) Patent No.: US 8,900,516 B2
(45) Date of Patent: Dec. 2, 2014

(54) METHOD OF ALTERING THE SENSITIVITY AND/OR SELECTIVITY OF A CHEMIRESISTOR SENSOR

(75) Inventors: Yvonne Joseph, Stuttgart (DE); Tobias Vossmeyer, Hamburg (DE); Akio Yasuda, Tokyo (JP)

(73) Assignee: Sony Deutschland GmbH, Berlin (DE)

( * ) Notice: Subject to any disclaimer, the term of this patent is extended or adjusted under 35 U.S.C. 154(b) by 1401 days.

(21) Appl. No.: 12/034,487

(22) Filed: Feb. 20, 2008

(65) Prior Publication Data

US 2008/0245675 A1      Oct. 9, 2008

(30) Foreign Application Priority Data

Mar. 30, 2007   (EP) .................................. 07006695

(51) Int. Cl.
*G01N 27/12*     (2006.01)
*G01N 27/04*     (2006.01)
*G01N 27/00*     (2006.01)
*B82Y 15/00*     (2011.01)

(52) U.S. Cl.
CPC ............... *G01N 27/125* (2013.01); *B82Y 15/00* (2013.01)
USPC .......... 422/82.02; 422/68.1; 422/50; 205/782

(58) Field of Classification Search
CPC ..... G01N 27/125; G01N 27/12; G01N 27/04; G01N 27/00
USPC ......................... 422/82.02, 68.1, 50; 205/782
See application file for complete search history.

(56) References Cited

U.S. PATENT DOCUMENTS 6,495,892 B2 * 12/2002 Goodman et al. ............ 257/414
2005/0129939 A1   6/2005 Shigematsu et al.

FOREIGN PATENT DOCUMENTS

| EP | 1 022 560 A1 | 7/2000 |
| EP | 1 215 485 A1 | 6/2002 |
| EP | 1 278 061 A1 | 1/2003 |
| WO | WO 03/018645 A1 | 3/2003 |
| WO | WO 03/046536 A1 | 6/2003 |

OTHER PUBLICATIONS

Werake, L.K.; Story, J.G.; Bertino, M.F.; Pillalamarri, S.K.; Blum, F. D. "Photolithographic synthesis of polyaniline nanofibres." Nanotechnology, 2005, 16, pp. 2833-2837.*
Mah, C.; Thurbide, K.B. "Acoustic methods of detection in gas chromatography." J. Sep. Sci, 2006, 29, pp. 1922-1930.*
Jinlou Gu, et al., "Thioether moiety functionalization of mesoporous silica films for the encapsulation of highly dispersed gold nanoparticles", Journal of Solid State Chemistry, vol. 179, No. 4, Apr. 2006, pp. 1060-1066.

* cited by examiner

*Primary Examiner* — Christine T Mui
(74) *Attorney, Agent, or Firm* — Oblon, Spivak, McClelland, Maier & Neustadt, L.L.P.

(57) ABSTRACT

The present invention relates to a method of altering the sensitivity and/or selectivity of a chemiresistor sensor, to a sensor and a sensor array produced by such method.

26 Claims, 7 Drawing Sheets

Chemical sensor: Thin chemosensitive film based on organically interlinked metal nanoparticles coated on a transducer

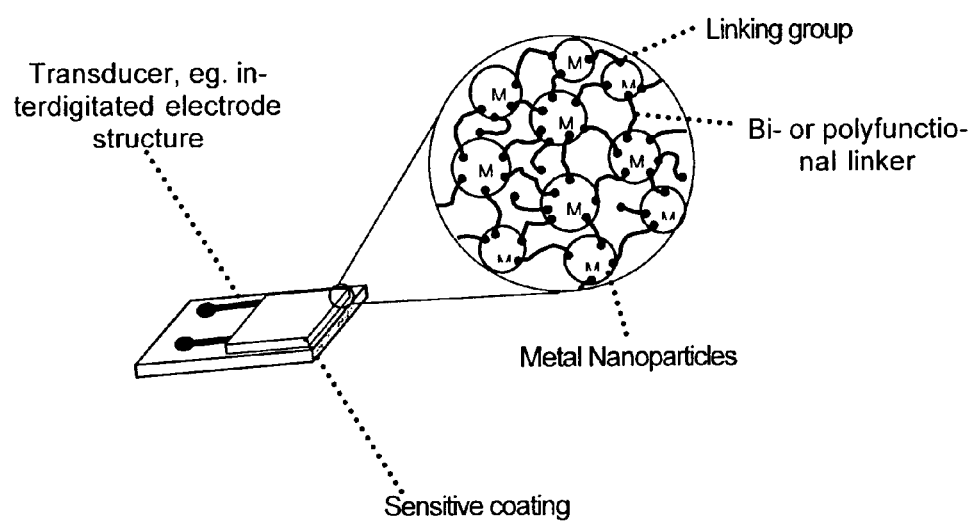
Fig. 1: Chemical sensor: Thin chemosensitive film based on organically interlinked metal nanoparticles coated on a transducer

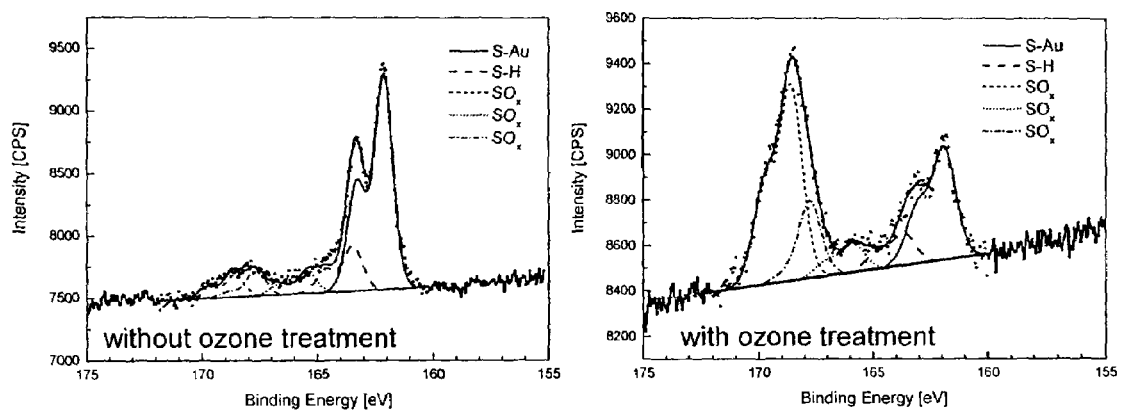
Fig. 2: Sulfur (2p) X-ray Photoelectron spectra of a chemiresistor coating with and without ozone treatment.

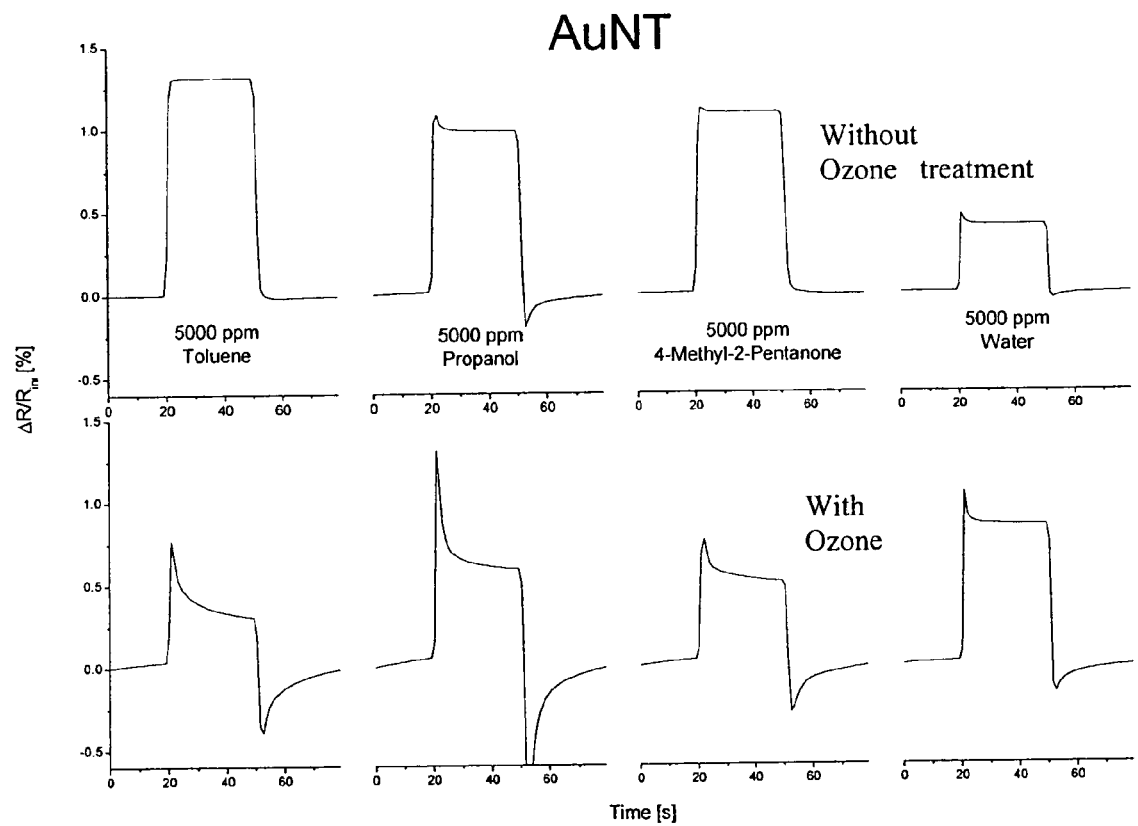
Fig. 3: Response traces towards the indicated analytes of nonanedithiol interlinked gold nanoparticles with and without ozone treatment (ozone generator)

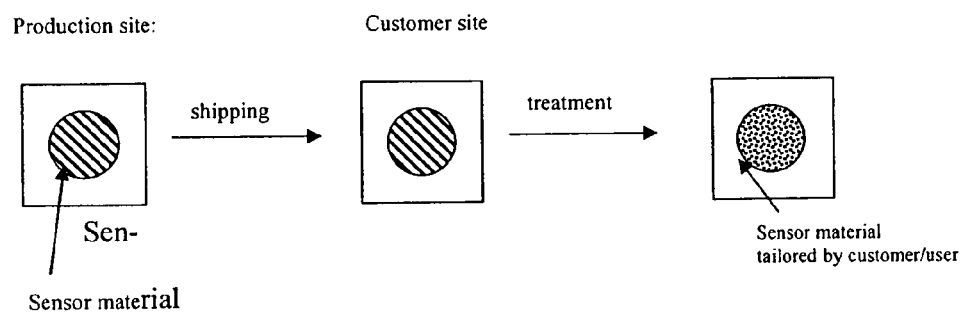
Fig. 4: Formation of a sensor by a treatment at the customer's/user's site.

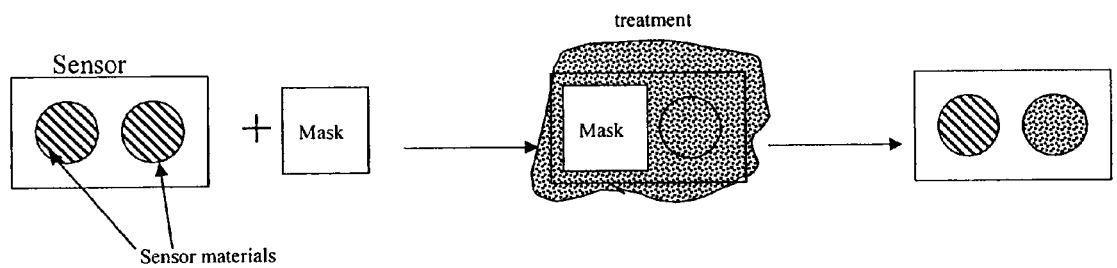
Fig. 5a: Formation of a sensor array with 2 different sensor materials from a sensor array with the same materials by a gas phase treatment

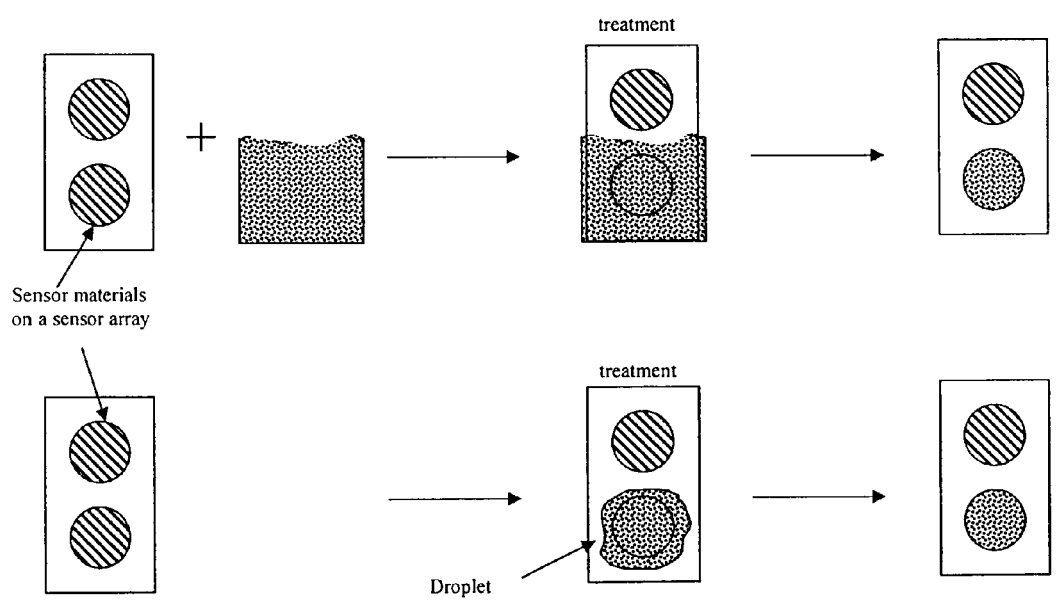
Fig. 5b: Formation of a sensor array with 2 different sensor materials from a sensor array with the same materials by a liquid phase treatment

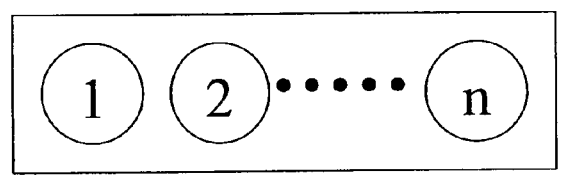
Sensor array with different materials
Fig 6. : Sensor array with different sensor materials 1-n formed by post preparation oxidation of a sensor array comprising only material 1. This means e.g. sensor 1= 0% oxidized groups, sensor 2= 10 % oxidized groups, sensor 3=... sensor n= 100% oxidized groups

METHOD OF ALTERING THE SENSITIVITY AND/OR SELECTIVITY OF A CHEMIRESISTOR SENSOR

CROSS-REFERENCE TO RELATED APPLICATIONS

The present application claims priority to European patent application EP 07006695.6, filed on Mar. 30, 2007.

FIELD OF THE INVENTION

The present invention relates to a method of altering the sensitivity and/or selectivity of a chemiresistor sensor, to a sensor and a sensor array produced by such method.

DISCUSSION OF THE BACKGROUND

Chemiresistor sensors for detection of analytes in the fluid phase (e.g. gas and vapour) based on conductive nanocomposite materials include an electrically conductive component that is dispersed in a non-conductive or semi-conductive medium. As conductive component metal nanoparticles, carbon black nanoparticles or conductive nanofibres may be used. The non-conductive component is typically an organic material, which acts as a continuous phase in which the conductive particles are distributed. The non-conductive material may also comprise functionalized organic molecules that serve either as capping ligands for the metal nanoparticles or to interlink the particles in a three-dimensional network.

The operating principle of these sensors comprises a measurement of the change in the film resistance caused by sorption of analytes in the composite material. It is believed that the sensitivity of the chemiresistor depends on the ability of the composite material to undergo volumetric change in presence of analytes. The chemical selectivity of the chemiresistors depends to a certain degree on the chemical composition and the presence of specific functionalities in the organic component of the nanocomposite material. Typically, the detection limit to analytes of these chemiresistors lies in the low parts-per-million (ppm) concentration range.

Numerous studies have been carried out with respect to improving the sensitivity and the chemical selectivity of inorganic/organic composite chemiresistors to analytes via modification of the chemical composition of the sensitive layer [1].

In addition, a combination of a plurality of different sensors to an array will enhance the recognition capability of the device. An example for such array, which is sometimes also referred to as "e-nose" is described in [2]

[1] EP1215485 describes a method for preparation of highly selective nanoparticle/organic interlinked sensors via introducing selectivity enhancing units in the linker molecules. Introducing an additional fine tuning unit in a close proximity of the selectivity-enhancing functionality can achieve a fine-tuning of the selectivity. WO9927357 describes a sensor based on films of thiol-encapsulated Au-nanoparticles where the selectivity of the sensor is tailored by introducing functionality to the ligand shell thereby providing active sites for sorption of target analytes. U.S. Pat. No. 6,290,911 discloses a method to tune the selectivity of carbon black/polymer chemiresistors by varying the composition of the organic component using blends of polymers and/or polymer/monomer mixtures.

[2] WO9908105 discloses techniques and systems for analyte detection. Here a sensor system (e-nose) comprising a sensor array, electrical readout, a preprocessor for the electrical signals combined with pattern recognition is described in detail.

Although the achievements in tailoring the selectivity of the aforementioned composite chemiresistor sensors described above are encouraging, there is still need of improvement. Up to now the sensitivity and selectivity of the chemiresistors are enhanced by designing new organic materials with desired chemical composition and functionality. This requires extensive and complicated chemical synthetic work. The preparation of chemiresistor arrays combining different sensitive materials in one device is even more difficult and expensive because patterning steps for each individual sensitive material are involved.

SUMMARY OF THE INVENTION

Accordingly, it was an object of the present invention to provide for a method for altering the sensitivity and/or selectivity of a chemiresistor sensor after fabrication of the sensor/sensor array. Moreover, it was an object of the present invention to provide for such method of altering the sensitivity and/or selectivity which method is easy to perform and reduces the fabrication costs. Moreover, it was an object of the present invention to provide for a method which is versatile and which may be used by the user of a chemiresistor sensor to adapt the sensor to the specific needs of the user's application. Furthermore it was an object of the present invention to provide for a method that allows the alteration of sensitivity and/or selectivity of chemiresistor sensors in a chemiresistor sensor array such that different selectivities and/or sensitivities of the individual sensors may be achieved.

The objects of the present invention are solved by a method of altering the sensitivity and/or selectivity of a chemiresistor sensor, said chemiresistor sensor comprising a sensitive layer having a plurality of electrically conducting or semiconducting particles embedded in an electrically non-conducting matrix, said sensitive layer comprising a plurality of oxidizable chemical functional groups, said method comprising the step:

subjecting said sensitive layer to an oxidation reaction.

DETAILED DESCRIPTION OF THE INVENTION

Preferably, said oxidation reaction is a controlled oxidation reaction and is not an undefined exposing said sensor to air.

In one embodiment said oxidation reaction is a reaction with a gas phase and/or a reaction with a liquid phase.

Preferably, said reaction involves anyone or several of the following gas phase reactions:

exposing said sensitive layer to air for a defined period of time, at a defined temperature of the air, wherein preferably said defined period of time is in the range of from 1 min to 300 min, and said defined temperature of the air is in the range of from 0° C. to 500° C., exposing said sensitive layer to ozone, exposing said sensitive layer to an oxygen plasma, exposing said sensitive layer to $SO_3$, exposing said sensitive layer to nitric oxides.

Preferably, said oxidation reaction involves anyone or several of the following liquid phase reactions:

exposing said sensitive layer to an aqueous solution of hydrogen peroxide exposing said sensitive layer to an aqueous solution of $KMnO_4$.

Preferably said exposing occurs under irradiation of said sensitive layer using electromagnetic radiation of wavelength in the range of from 180-1200 nm.

In one embodiment said exposing to ozone, oxygen plasma, $SO_3$, nitric oxides occurs for a period of time in the range of from 1 s to 600 s.

Preferably, within said sensitive layer, said oxidizable chemical functional groups are oxidized by said oxidation reaction, wherein, more preferably, only a proportion of said plurality of oxidizable chemical functional groups are oxidized by said oxidation reaction, wherein, even more preferably, said proportion is ≥20%, more preferably ≥40%, more preferably ≥60% and most preferably ≥80%.

In one embodiment said electrically conducting or semiconducting particles are particles having an average diameter<1 μm, preferably <500 nm, more preferably <300 nm, and most preferably <100 nm, wherein, preferably, said particles are metal particles or semiconductor particles, and wherein, more preferably, said particles are selected from the group comprising metal particles, i.e. noble metal particles such as Au, Pt, Ag, Pd, coinage metal particles such as Cu, Ni, Fe, combinations of these metals in single nanoparticles, e.g. an alloy or core/shell metal nanoparticles; semiconductive nanoparticles, e.g. II/VI semiconductors such as CdS, CdSe, CdTe, ZnS, ZnSe, ZnTe, HgS, HgSe, HgTe, or III/V semiconductors such as GaAs, InP; conducting or semiconducting nanoparticles from organic materials, such as conductive polymers; conductive particles, such as carbon black particles or metal-decorated carbon black particles, e.g. Pt/carbon black or PtRu/carbon black nanoparticles.

In one embodiment said electrically non-conducting matrix is a network of bi- or polyfunctional linker molecules and said particles are interlinked with said linker molecules, or said electrically non-conducting matrix is a network of mono-, bi- or polyfunctional ligand molecules and said particles are capped by said ligand molecules.

Preferably, said electrically non-conducting matrix is made of at least one polymer, wherein, more preferably, said polymer is selected from the group comprising poly(amide), poly(amido amine), poly(propylene imine), poly(phenylene), poly(ethylene oxide), poly(ethylene imine), hyperbranched poly(ethylene imine) poly(N-isopropyl acrylamide), poly(ethylene glycol), poly(vinyl pyrrolidone), poly(styrene), poly(vinyl alcohol), poly(4-vinyl phenol), poly(epichchlorohydrin), poly(isobutylene), poly(vinyl acetate), poly(methyl methacrylate), poly(caprolactone) fluoropolyols, polysiloxanes, polyaniline, polythiophene, polypyrrol, or copolymers like poly(ethylene oxide)-co-poly(amido amine), poly(ethylene-co-vinyl acetate), poly(styrene-co-allyl alcohol), poly(vinyl chloride-co-vinyl acetate), poly(styrene-co-maleic anhydride), poly(vinyl methyl ester-co-maleic anhydride) and combinations thereof.

In one embodiment said method is applied to a chemiresistor sensor array of a plurality of chemiresistor sensors as defined above, each sensor having a sensitive layer as defined above, wherein said sensitive layers of different sensors are subjected to an oxidation reaction to varying degrees, wherein, preferably, some sensitive layers are protected from said oxidation reaction and do not become subjected to said oxidation reaction, and wherein, more preferably, some sensitive layers are protected by anyone or any combination of the following:
  using a mask to cover the sensitive layer,
  not exposing the sensitive layer to oxidizing conditions, e.g. by not immersing said sensitive layer into an oxidizing solution, not exposing said sensitive layer to an oxidizing gas.

In one embodiment within said chemiresistor sensor array, different sensitive layers become oxidized to varying degrees such that different sensitive layers have different proportions of oxidizable chemical functional groups oxidized, as a result of the oxidation reaction, wherein, preferably, within said chemiresistor sensor array, some sensitive layers have 0% oxidizable groups oxidized, some sensitive layers have ≥20% oxidizable groups oxidized, some sensitive layers have ≥40% oxidizable groups oxidized, some sensitive layers have ≥60% oxidizable groups oxidized, some sensitive layers have ≥80% oxidizable groups oxidized, and some sensitive layers have all of their oxidizable groups oxidized.

The objects of the present invention are also solved by a chemiresistor sensor produced by the method according to the present invention.

The objects of the present invention are also solved by a chemiresistor sensor array produced by the method according to the present invention, wherein all individual sensors are treated in the same manner or wherein at least some of the individual sensors are treated differently, i.e. oxidised to different extents.

The inventors have surprisingly found that by performing an oxidation reaction on the sensitive layer of a chemiresistor sensor, the sensitivity and/or selectivity of such sensor may become drastically altered. For example, by performing an oxidation reaction on such a sensor, the sensitivity towards hydrophobic analytes may become decreased and the sensitivity towards hydrophilic analytes may become increased. As a result thereof, the selectivity of the respective sensor is changed. Performing such an oxidation reaction usually is simple to perform and can be done using standard equipment that is commonly available in a chemical laboratory. Since the performance of an oxidation reaction depends on the presence of chemical functional groups that can be oxidised ("oxidisable groups"), the oxidation reaction can be tailored and controlled in accordance with the present invention such that only a proportion of all of the oxidisable groups in a single sensor may become oxidised, or within a chemiresistor sensor array, different sensors may become oxidised to different extents, thus providing for different chemiresistor sensors having different sensitivities and/or selectivities.

The term "analyte sensitive layer" or "sensitive layer", as used herein, is meant to designate a layer which, in response to the presence of an analyte, yields a measurable signal that can be detected by conventional means, for example by measuring the chemical resistance of this layer.

The term "nanoparticles", as used herein, is meant to designate particles which have characteristic dimensions<1 μm. Further, such nanoparticles can have different shapes, i.e. faceted (spherical), rod-like, disc-like, or fractal, e.g. multi-pod, star-like, spiky. Typically, the characteristics diameter of these nanoparticles at an average is <1 μm, preferably ≤500 nm, more preferably ≤300 nm. In a preferred embodiment said particles have an average diameter in the range of from 1 nm to 100 nm, most preferably from 1 nm to 50 nm. However, the actual size of the respective nanoparticles also depends on the respective analyte to be detected, since the size of a nanoparticles may also determine and/or affect its chemical selectivity towards specific analytes. In no case, however, will the dimension of said nanoparticles be >1 μm. In turn, particles complying with the aforementioned dimension requirements may also be referred to as "nanoparticles" within the present application.

The term "a proportion of said oxidisable chemical functional groups are oxidised" is meant to signify that, if one considers all of the oxidisable chemical functional groups present on such sensitive layer as 100%, a proportion thereof will be a fraction of such 100%, and it is such fraction which becomes oxidized by a reaction in accordance with the present invention. For example, the proportion of chemical groups oxidised in accordance with the present invention in a sensor may be ≥20%, which means that at least 20% of all oxidisable chemical functional groups present in the sensitive layer of such sensor have become oxidised by the method according to the present invention. Likewise, in a chemiresistor sensor array, different sensors and their respective sensitive layers may become subject to different oxidation reactions or to oxidation reactions at different extents such that, effectively, one sensor within the array may have ≥10% of its oxidisable groups oxidised, whereas another sensor within the same array may have 0% of its oxidisable groups oxidised, and yet another sensor within the same array may have ≥80% of its oxidisable groups oxidised. In this way, an array which originally had the same sensitivity in all the sensors present therein can be transformed to an array of sensors wherein each sensor has a different sensitive property.

As used herein, the term "oxidation" is meant to denote a process wherein the entity becoming oxidised releases electrons. In a more specific sense, the term "oxidation" is meant to refer to a reaction wherein oxygen is involved and an oxide is produced.

In the chemiresistors according to the present invention, the electrically conducting or semiconducting particles are embedded in a non-conducting matrix. Such non-conducting matrix in one embodiment is preferably polymeric. In another embodiment said non-conducting matrix is formed by organic linker molecules which link the electrically conductive or semi-conductive particles with each other, or it is formed by organic ligand molecules which function as capping groups to said electrically conductive or semi-conductive particles. Suitable organic linker molecules and organic ligand molecules are for example disclosed in European Patent Application No. 00 127 149.3 and European Patent Application No. 05 025 558.7, both of which are incorporated in their entirety by reference thereto.

As used herein, the term "electrically conductive" refers to the capability of transporting electrons or holes. An "electrically non-conductive" polymer is a polymer incapable of such transport.

The methods by which an analyte sensitive layer can be created are known to someone skilled in the art and have also been for example described in EP 1 215 485 A1. They may for example be prepared by layer-by-layer-deposition, which involves the repeated sequential immersion of a substrate into a dispersion of nanoparticles/nanofibres and a solution of organic component (e.g. the polymers making up the organic polymeric matrix or linker molecules) and subsequent drying. Other possibilities of creating the analyte sensitive layer includes spin coating technique, drop casting techniques, spray coating techniques, ink-jet printing, stamping, ligand exchange precipitation from solution, Langmuir-Blodgett and Langmuir-Schäffer-techniques.

The chemiresistor sensors in accordance with the present invention are capable of detecting an analyte in the "fluid phase", which term, as used herein is meant to include both liquid phase and gas phase.

Without wishing to be bound by any theory, the present inventors attribute the success of the method according to the present invention to the presence of oxidisable chemical functional groups within the analyte sensitive layer of a chemiresistor sensor.

Sensitive coatings based on organically encapsulated conducting particles (e.g. carbon black embedded in polymers, or metal nanoparticles interlinked in an organic matrix, etc.) that can be altered by a chemical oxidation treatment have to expose functional groups containing carbon, oxygen, sulfur or nitrogen. Well known examples for such kind of oxidizable functional groups are:

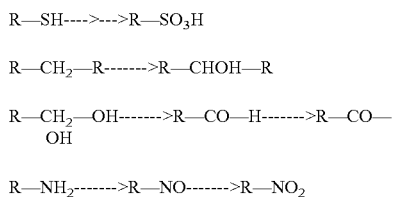

Other examples for possible conversions of functional groups or the detailed reaction procedures are given in known text books of organic chemistry (such as "Organic Chemistry", Salomons, $4^{th}$ ed., 1988, Wiley; "Advanced Organic Chemistry", March, $3^{rd}$ ed., 1985, Wiley, "Organische Chemie", Vollhardt, 1. ed., 1988, VCH, Verlagsgesellschaft) which are incorporated in their entirety by reference thereto.

The oxidation reaction in accordance with the present invention can be a gas phase reaction or a reaction with a liquid phase. Possible gas phase methods for oxidation include but are not limited to exposing the materials to air, to ozone, to an oxygen plasma, to $SO_3$ or nitric oxides. The liquid phase reaction can be performed by putting the sensor in the liquid (e.g. immersion) or by putting the liquid on the sensor (e.g. droplets by ink-jet printing, spraying etc.). A wet chemical oxidation includes but is not limited to the reaction with hydrogen peroxide. To alter a sensor material not only one oxidation can be applied exclusively, also a variety of reactions can be applied one after the other. Also the intensity of the oxidation treatment can be varied, by changing the time, temperature or stoichiometry of the treatment.

A specially preferred material, which can be oxidized, is a sensitive coating comprising metal nanoparticles interlinked with bi- or polyfunctional organic molecules prepared by layer by layer self assembly (compare FIG. 1 below and EP1022560).

BRIEF DESCRIPTION OF THE FIGURES

In the following, reference is made to the figures, wherein

FIG. 1 shows a chemiresistor sensor, wherein a thin chemosensitive film ("sensitive layer") is based on organically interlinked metal nanoparticles coated on a transducer, FIG. 2 shows sulfur (2p) X-ray photoelectron spectra of a chemiresistor coating with and without ozone treatment, FIG. 3 shows response traces towards the indicated analytes of nonanedithiol interlinked gold nanoparticles with and without ozone treatment (ozone generator), FIG. 4 shows the formation/modification of a sensor by a post-fabrication treatment (oxidation) at the end-user's side, FIG. 5a shows the fabrication of a sensor array with 2 different sensor materials from a sensor array with the same materials by a gas phase treatment, wherein one of the sensors is covered by a mask and thereby protected from the gas phase treatment, FIG. 5b shows the fabrication of a sensor array with 2 different sensor materials from a sensor array with the same materials by a liquid phase treatment, again, where only one sensor is exposed to such treatment, by immersing it in the appropriate treatment solution or by exposing it to an appropriate droplet of such solution, whereas the other sensor is not exposed to such treatment, FIG. 6 shows a sensor array with different sensor materials denoted by the numerals 1, 2, 3, . . . n, formed by post-preparative oxidation of a sensor array originally comprising only one material, wherein the different sensors have been oxidised to different extents such that one sensor has 0% oxidised groups, another sensor has 10% oxidised groups, another sensor has 20% oxidised groups, . . . and sensor n has 100% oxidised groups.

Moreover, reference is made to the following examples which are given to illustrate, not to limit the present invention.

EXAMPLES

Example 1

Amongst various materials, gold nanoparticles interlinked with organic poly- or dithiols are especially suited. These were prepared as described in EP 00 127 149 and EP 05 025 558.7. In the simplest case of an interlinking alkylenedithiol, the functional SH groups can be oxidized e.g. by an ozone treatment.

The X-ray photoelectron spectra of nonanedithiol interlinked gold nanoparticles, prepared by layer by layer self-assembly (shown in FIG. 2) reveal mostly Au—S—R and R—S—H before and Au—$SO_x$ after treatment with Ozone (1 min ozone exposure in an UVO-Cleaner, Model no. 42-220, Jelight Company Inc., CA, USA). Due to the treatment the sensitivity and selectivity of the sensor changed (compare FIG. 3).

FIG. 2 shows Sulfur (2p) X-ray Photoelectron spectra of a chemiresistor coating with and without ozone treatment. Ozone treatment was performed by generating ozone in-situ.

As can be seen in FIG. 3 which shows response traces towards the indicated analytes of nonanedithiol interlinked gold nanoparticles with and without ozone treatment (ozone generator), the sensitivity towards hydrophobic analytes decreases and the sensitivity towards hydrophilic analytes increased. Thus the selectivity is changed.

Example 2

A comparable effect can be achieved by oxidative treatment of the sensor by immersing the chemiresistor in e.g. 5% hydrogen peroxide solution for 1-60 seconds.

Example 3

For single sensor devices, this post-preparation treatment allows the selectivity adjustment of a sensor at a place different from the sensor fabrication place and at a time distinctly later than original manufacture. This means that possibly a customer or technician or any end-user can adapt the sensor to the specific needs at the end-user's site (compare FIG. 4).

Special treatment kits comprising different chemicals can be used to make the adjustment easy.

Example 4

The method of adjusting the selectivity is not limited to devices comprising one sensor, also multi sensor devices can be treated and thus adjusted, resulting in a sensor array suitable to be implemented in "e-noses".

In this case, a sensor array comprising identical sensitive material in all sensors can be transformed into an array of sensors consisting of materials with different sensitive properties by oxidative treatments as described above. Here, by excluding some sensors from the reaction conditions on the same multi sensor device (e.g. by simply covering some of them with a mask, or immersing not all of them in the reaction solution), sensor arrays can be altered easily. This is shown in FIGS. 5 a) and b).

The resulting sensor array is shown in FIG. 6. Here, all sensors of the array had the same material in their respective sensitive layer. For some sensors this material was altered by different oxidation conditions. This results in a sensor array comprising sensors with chemosensitive coatings with different concentration of oxidized functional groups. This can be seen in FIG. 6 which shows a sensor array with different sensor materials "1"-"n" formed by post-preparation oxidation of a sensor array comprising only material 1. This means e.g. sensor/sensitive material 1=0% of oxidized groups, sensor/sensitive material 2=10% of oxidized groups, sensor/sensitive material 3= . . . , sensor/sensitive material n=100% of oxidized groups.

In this method, the number of different sensor materials which may thus be created in one sensor array is theoretically unlimited. Also a combinatorial approach can be applied. Lithographic methods may support the combinatorial approach.

The features of the present invention disclosed in the specification, the claims and/or in the accompanying drawings, may, both separately, and in any combination thereof, be material for realising the invention in various forms thereof.

The invention claimed is:

1. A method of altering the sensitivity and/or selectivity of a chemiresistor sensor, wherein said chemiresistor sensor comprises a sensitive layer comprising:
   a plurality of electrically conducting or semiconducting particles embedded in an electrically non-conducting matrix; and
   a plurality of oxidizable chemical functional groups, wherein said method comprises:
   subjecting said sensitive layer to a post-fabrication oxidation reaction whereby at least 20% of said plurality of oxidizable chemical functional groups are oxidized by said post-fabrication oxidation reaction.

2. The method according to claim 1, wherein said post-fabrication oxidation reaction is a controlled post-fabrication oxidation reaction and is not an undefined exposing said sensor to air.

3. The method according to claim 1, wherein said post-fabrication oxidation reaction is a reaction with a gas phase and/or a reaction with a liquid phase.

4. The method according to claim 1, wherein said post-fabrication oxidation reaction comprises one or more of the following gas phase reactions:
   exposing said sensitive layer to air for a defined period of time, at a defined temperature of the air, wherein said defined period of time is in the range of from 1 min to 300 min, and wherein said defined temperature of the air is in the range of from 0° C. to 500° C.,
   exposing said sensitive layer to ozone,
   exposing said sensitive layer to an oxygen plasma,
   exposing said sensitive layer to $SO_3$, and
   exposing said sensitive layer to a nitric oxide.

5. The method according to claim 1, wherein said post-fabrication oxidation reaction comprises one or more of the following liquid phase reactions:
   exposing said sensitive layer to an aqueous solution of hydrogen peroxide, and
   exposing said sensitive layer to an aqueous solution of $KMnO_4$.

6. The method according to claim 4, wherein any one or more of said exposing comprises irradiating said sensitive layer with electromagnetic radiation having a wavelength in the range of from 180 nm to 1200 nm.

7. The method according to claim 4, wherein any one or more of said exposing to ozone, oxygen plasma, $SO_3$, and nitric oxide occurs for a period of time in the range of from 1 s to 600 s.

8. The method according to claim 1, wherein at least 40% of said plurality of oxidizable chemical functional groups are oxidized by said post-fabrication oxidation reaction.

9. The method according to claim 1, wherein said electrically conducting or semiconducting particles are particles having an average diameter of <1 μm.

10. The method according to claim 9, wherein said particles are metal particles or semiconductor particles.

11. The method according to claim 10, wherein said particles are selected from the group consisting of:
   metal particles, noble metal particles, Au particles, Pt particles, Ag particles, Pd particles, coinage metal particles, Cu particles, Ni particles, Fe particles, combinations of these metals in single nanoparticles, and alloy or core/shell metal nanoparticles;
   semiconductive nanoparticles, semiconductive nanoparticles of II/VI semiconductors, CdS nanoparticles, CdSe nanoparticles, CdTe nanoparticles, ZnS nanoparticles, ZnSe nanoparticles, ZnTe nanoparticles, HgS nanoparticles, HgSe nanoparticles, HgTe nanoparticles, semiconductive nanoparticles of III/V semiconductors, GaAs nanoparticles, InP nanoparticles;
   conducting or semiconducting nanoparticles of organic materials, conductive polymers; and
   conductive carbon black particles, conductive metal-decorated carbon black particles, conductive Pt/carbon black and conductive PtRu/carbon black nanoparticles.

12. The method according to claim 1, wherein said electrically non-conducting matrix is a network of bi- or polyfunctional linker molecules and said electrically conducting or semiconducting particles are interlinked with said linker molecules.

13. The method according to claim 1, wherein said electrically non-conducting matrix comprises at least one polymer.

14. The method according to claim 13, wherein said polymer is selected from the group consisting of poly(amide), poly(amido amine), poly(propylene imine), poly(phenylene), poly(ethylene oxide), poly(ethylene imine), hyperbranched poly(ethylene imine) poly(N-isopropyl acrylamide), poly (ethylene glycol), poly(vinyl pyrrolidone), poly(styrene), poly(vinyl alcohol), poly(4-vinyl phenol), poly(epichlorohydrin), poly(isobutylene), poly(vinyl acetate), poly(methyl methacrylate), poly(caprolactone) fluoropolyols, polysiloxanes, polyaniline, polythiophene, polypyrrol, or copolymers like poly(ethylene oxide)-co-poly(amido amine), poly(ethylene-co-vinyl acetate), poly(styrene-co-allyl alcohol), poly(vinyl chloride-co-vinyl acetate), poly(styrene-co-maleic anhydride), poly(vinyl methyl ester-co-maleic anhydride) and combinations thereof.

15. The method according to claim 1, wherein said method is applied to a chemiresistor sensor array comprising a plurality of said chemiresistor sensors, wherein said sensitive layers of said chemiresistor sensors are subjected to said post-fabrication oxidation reaction to varying degrees.

16. The method according to claim 15, wherein one or more sensitive layers are protected from said post-fabrication oxidation reaction and do not become subjected to said post-fabrication oxidation reaction.

17. The method according to claim 16, wherein one or more sensitive layers are protected by one or more of the following:
   using a mask to cover the sensitive layer,
   not exposing the sensitive layer to oxidizing conditions,
   not immersing said sensitive layer into an oxidizing solution, and
   not exposing said sensitive layer to an oxidizing gas.

18. The method according to claim 15, wherein within said chemiresistor sensor array, different sensitive layers become oxidized to varying degrees such that different sensitive layers have different proportions of oxidizable chemical functional groups oxidized as a result of the post-fabrication oxidation reaction.

19. The method according to claim 18, wherein within said chemiresistor sensor array, one or more sensitive layers have ≥20% oxidizable groups oxidized, one or more sensitive layers have ≥40% oxidizable groups oxidized, one or more sensitive layers have ≥60% oxidizable groups oxidized, one or more sensitive layers have ≥80% oxidizable groups oxidized, and one or more sensitive layers have all of their oxidizable groups oxidized.

20. A chemiresistor sensor produced by the method according to claim 1.

21. A chemiresistor sensor array produced by the method according to claim 15.

22. The method according to claim 5, wherein said exposing comprises irradiating said sensitive layer with electromagnetic radiation having a wavelength in the range of from 180 nm to 1200 nm.

23. The method according to claim 1, wherein at least 80% of said plurality of oxidizable chemical functional groups are oxidized by said post-fabrication oxidation reaction.

24. The method according to claim 1, wherein said electrically conducting or semiconducting particles are particles having an average diameter of <100 nm.

25. The method according to claim 1, wherein said electrically non-conducting matrix is a network of mono-, bi- or polyfunctional ligand molecules and said particles are capped by said ligand molecules.

26. The method according to claim 18, wherein said chemiresistor sensor array further comprises one or more sensitive layers have 0% oxidizable groups oxidized.

* * * * *